US00PP14263P29

(12) United States Plant Patent
Dettmer et al.

(10) Patent No.: US PP14,263 P2
(45) Date of Patent: Nov. 4, 2003

(54) AZALEA PLANT NAMED 'MISS LULU'

(50) Latin Name: *Rhododendron simsii*
Varietal Denomination: Miss Lulu

(75) Inventors: Peter Dettmer, Sassenburg (DE); Eleonore Dettmer, Sassenburg (DE)

(73) Assignee: Eleonore Dettmer und Peter Dettmer GbR, Sassenburg (DE)

( * ) Notice: Subject to any disclaimer, the term of this patent is extended or adjusted under 35 U.S.C. 154(b) by 0 days.

(21) Appl. No.: 10/259,966

(22) Filed: Sep. 29, 2002

(51) Int. Cl.[7] ..... A01H 5/00
(52) U.S. Cl. ..... Plt./239
(58) Field of Search ..... Plt./238, 239, 240

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Azalea plant named 'Miss Lulu', characterized by its upright and outwardly spreading plant habit; glossy and very dark green-colored leaves; freely branching habit; pink-colored double flowers; and excellent postproduction longevity.

1 Drawing Sheet

Botanical classification/cultivar designation: *Rhododendron simsii* 'Miss Lulu'.

BACKGROUND OF THE INVENTION

The present Invention relates to a new and distinct cultivar of Azalea, botanically known as *Rhododendron simsii*, and hereinafter referred to by the name 'Miss Lulu'.

The new Azalea is a product of a planned breeding program conducted by the Inventors in Sassenburg, Germany. The objective of the breeding program is to create new strong Azalea cultivars with excellent postproduction longevity.

The new Azalea originated from a cross-pollination made by the Inventors in January, 1993, in a controlled environment in Sassenburg, Germany, of the *Rhododendron simsii* cultivar St. Valentine, not patented, as the female, or seed, parent with an unidentified selection of *Rhododendron simsii*, not patented, as the male, or pollen, parent. The new Azalea was discovered and selected by the Inventors as a flowering plant within the progeny of the stated cross in a controlled environment in Sassenburg, Germany.

Asexual reproduction of the new Azalea by terminal cuttings taken in a controlled environment in Sassenburg, Germany since May, 1996, has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Miss Lulu'. These characteristics in combination distinguish 'Miss Lulu' as a new and distinct cultivar:

1. Upright and outwardly spreading plant habit.
2. Glossy and very dark green-colored leaves.
3. Freely branching habit.

4. Pink-colored double flowers.
5. Excellent postproduction longevity.

Compared to plants of the female parent, the cultivar St. Valentine, plants of the new Azalea have better foliage longevity and flower for a longer period of time. Plants of the new Azalea differ from plants of the male parent primarily in flower color.

Plants of the new Azalea can be compared to the plants of the cultivar Theo, disclosed in U.S. Plant Pat. No. 10,523. However, in side-by-side comparisons conducted in Sassenburg, Germany, plants of the new Azalea differed from plants of the cultivar Theo in the following characteristics:

1. Plants of the new Azalea were more compact and not as open in growth habit as plants of the cultivar Theo.
2. Plants of the new Azalea had more elongated flower buds than plants of the cultivar Theo.
3. Flowers of plants of the new Azalea were double in form whereas flowers of plants of the cultivar Theo were semi-double in form.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the colors of the new Azalea.

The photograph at the top of the sheet comprises a side perspective view of a typical flowering plant of 'Miss Lulu'.

The photograph at the bottom of the sheet is a close-up view of typical leaves and flowers of 'Miss Lulu'.

DETAILED BOTANICAL DESCRIPTION

The aforementioned photographs and following observations and measurements describe plants grown in Sassenburg, Germany in a glass-covered greenhouse under commercial production conditions. During the production of the plants, day temperatures were about 16° C. and night temperatures were about 10° C. Plants were pinched three times during the production of the plants. Plants used for the photographs and description were about 22 months from planting rooted young plants.

In the following description, color references are made to The Royal Horticultural Society Colour Chart, 1995 Edition, except where general terms of ordinary dictionary significance are used.

Botanical classification: *Rhododendron simsii* 'Miss Lulu'.

Parentage:

*Female or seed parent.*—*Rhododendron simsii* cultivar St. Valentine, not patented.

*Male or pollen parent.*—Unidentified selection of *Rhododendron simsii*, not patented.

Propagation:

*Type.*—By vegetative cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Fine; mostly white in color.

*Rooting habit.*—Freely branching.

Plant description:

*Plant form and growth habit.*—Perennial, evergreen; upright and outwardly spreading plant habit; inverted triangle; uniform and symmetrical plant habit; moderately vigorous growth habit. Densely foliated. Freely flowering; numerous flowers per plant.

*Branching habit.*—Freely branching; about six lateral branches develop after pinching (removal of terminal apex). Plant height, soil level to top of flowers: About 22 cm. Plant diameter, area of spread: About 35 cm.

*Lateral branch description.*—Length: About 20 cm. Diameter at base: About 4 mm. Texture: Sparsely pubescent. Color: Young: 146D. Mature: 200A.

*Foliage description.*—Arrangement: Alternate, single. Length: About 3 to 6 cm. Width: About 1 to 2.5 cm. Shape: Elliptic. Apex: Mucronate. Base: Attenuate. Margin: Entire. Venation pattern: Pinnate. Texture, upper and lower surfaces: Leathery; pubescent. Color: Young foliage, upper surface: 137A; glossy. Young foliage, lower surface: Close to 146B. Fully expanded foliage, upper surface: Darker than 147A; glossy. Fully expanded foliage, lower surface: Close to 147B. Petiole: Length: About 1 cm. Diameter: About 3 mm. Color, upper and lower surfaces: Close to 146D.

Flower description:

*Natural flowering season.*—Spring after sufficient cool period. Flowers persistent.

*Flower arrangement.*—Double flowers arranged singly at terminals with usually about four to five flowers per apex; freely flowering. Flowers face upward and outward. Flowers not fragrant.

*Flower diameter.*—About 6 cm.

*Flower depth.*—About 2.5 cm.

*Postproduction longevity.*—Plants maintain good flower substance for more than four weeks.

*Flower bud* (*before showing color*).—Rate of opening: About three to four days depending on temperatures. Length: About 1 cm. Diameter: About 8 mm. Shape: Ovoid. Color: 62D.

*Petals.*—Arrangement: Double flower form; one outer whorl of five or six fused petals surrounding five or six petaloid structures that are irregular in size. Length, petals: About 3.2 cm. Width, petals: About 2.3 cm. Shape, petals and petaloids: Obovate. Apex, petals and petaloids: Broadly acute. Base, petals and petaloids: Fused. Margin, all petals: Entire. Texture, upper and lower surfaces: Smooth, velvety. Color: When opening, upper surface: 75C. When opening, lower surface: 65B. Fully opened, upper surface: 68B; towards base and margins, 69D to close to 155D. Fully opened, lower surface: 73C to 73D.

*Sepals.*—Arrangement/appearance: Single whorl of five sepals fused towards base into a star-shaped calyx. Length: About 4 to 5 mm. Width: About 2 to 3 mm. Shape: Ovate. Apex: Acute. Margin: Entire. Texture, upper and lower surfaces: Smooth, glabrous. Color, upper and lower surfaces: 145C.

*Peduncles.*—Length: About 9 mm. Diameter: About 2 mm. Angle: Mostly upright. Strength: Flexible; strong. Texture: Pubescent. Color: 145C.

*Reproductive organs.*—Androecium: Stamens transformed into petaloid structures; occasionally one or two true stamens. Anther length: About 2 mm. Anther shape: Oblong. Anther color: Close to 59A. Amount of pollen: None observed. Gynoecium: Quantity of pistils: One per flower. Pistil length: About 3 cm. Style length: About 2.8 mm. Style color: 11D. Stigma shape: Rounded. Stigma color: Close to 144B. Ovary color: 145C; heavily whiskered.

*Fruit/seed.*–Fruit and seed production has not been observed.

Temperature tolerance: Plants of the new Azalea have been observed to tolerate temperatures from 2 to 38° C.

Disease/pest resistance: Plants have not been observed to be resistant to pathogens and pests common to Azaleas.

It is claimed:

1. A new and distinct Azalea plant named 'Miss Lulu', as illustrated and described.

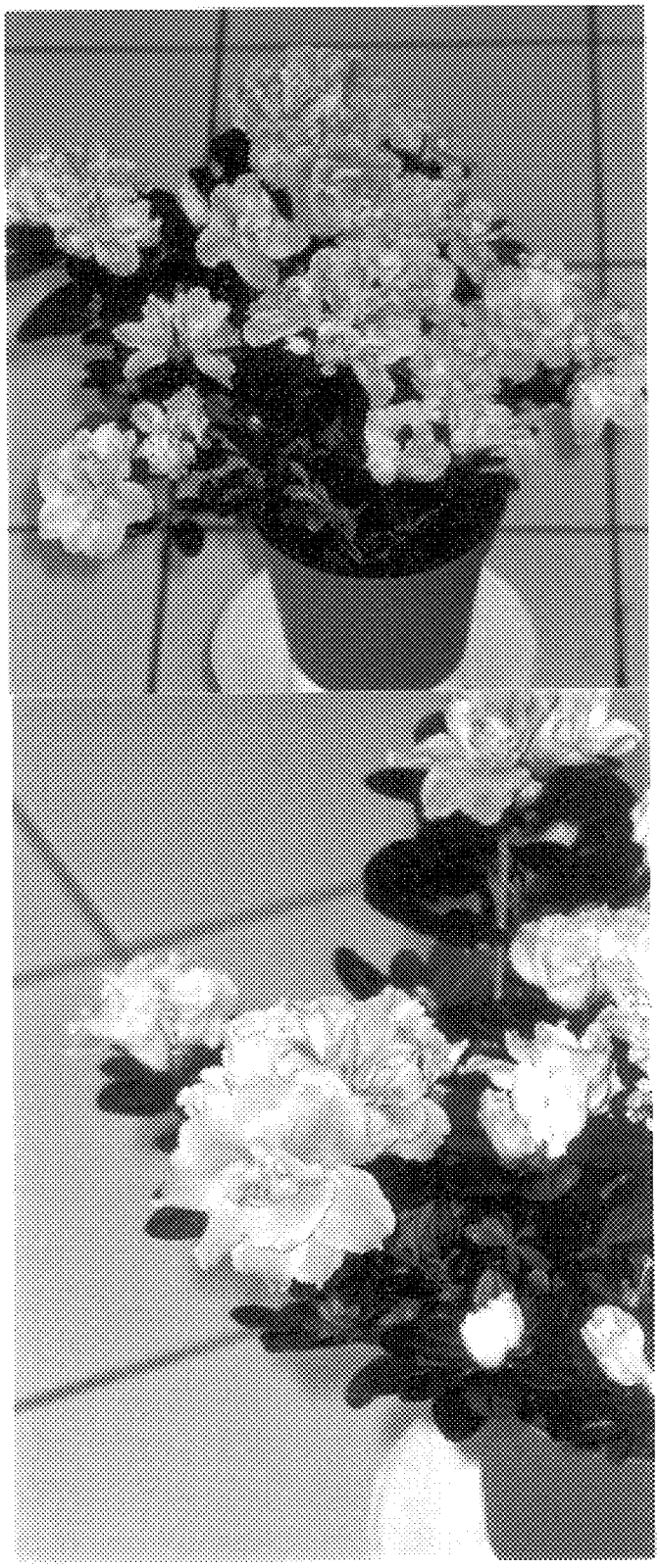

* * * * *